US011237162B2

(12) United States Patent
Masuda et al.

(10) Patent No.: US 11,237,162 B2
(45) Date of Patent: Feb. 1, 2022

(54) COMPOSITE PARTICLES, COATED PARTICLES, METHOD FOR PRODUCING COMPOSITE PARTICLES, LIGAND-CONTAINING SOLID PHASE CARRIER AND METHOD FOR DETECTING OR SEPARATING TARGET SUBSTANCE IN SAMPLE

(71) Applicants: JSR CORPORATION, Minato-ku (JP); JSR LIFE SCIENCES CORPORATION, Minato-ku (JP); JSR LIFE SCIENCES, LLC, Sunnyvale, CA (US); JSR Micro N.V., Leuven (BE)

(72) Inventors: Takeaki Masuda, Minato-ku (JP); Shunsuke Onogi, Minato-ku (JP)

(73) Assignees: JSR CORPORATION, Minato-ku (JP); JSR LIFE SCIENCES CORPORATION, Minato-ku (JP); JSR LIFE SCIENCES, LLC, Sunnyvale, CA (US); JSR Micro N.V., Leuven (BE)

( * ) Notice: Subject to any disclaimer, the term of this patent is extended or adjusted under 35 U.S.C. 154(b) by 299 days.

(21) Appl. No.: 16/303,941

(22) PCT Filed: May 23, 2017

(86) PCT No.: PCT/JP2017/019166
§ 371 (c)(1),
(2) Date: Nov. 21, 2018

(87) PCT Pub. No.: WO2017/204209
PCT Pub. Date: Nov. 30, 2017

(65) Prior Publication Data
US 2020/0319171 A1 Oct. 8, 2020

(30) Foreign Application Priority Data

May 24, 2016 (JP) .............................. JP2016-103569

(51) Int. Cl.
| G01N 33/545 | (2006.01) |
| G01N 33/543 | (2006.01) |
| G01N 33/553 | (2006.01) |
| B82Y 40/00  | (2011.01) |
| C08F 2/56   | (2006.01) |
| C08F 12/06  | (2006.01) |
| C08F 220/06 | (2006.01) |
| H01F 41/02  | (2006.01) |
| H01F 1/36   | (2006.01) |
| H01F 1/00   | (2006.01) |
| C08F 2/22   | (2006.01) |

(52) U.S. Cl.
CPC ............ *G01N 33/545* (2013.01); *B82Y 40/00* (2013.01); *C08F 2/22* (2013.01); *C08F 2/56* (2013.01); *C08F 12/06* (2013.01); *C08F 220/06* (2013.01); *G01N 33/54326* (2013.01); *G01N 33/54346* (2013.01); *G01N 33/553* (2013.01); *H01F 1/0063* (2013.01); *H01F 1/36* (2013.01); *H01F 41/0253* (2013.01); *G01N 2446/40* (2013.01)

(58) Field of Classification Search
CPC ......... B82Y 40/00; H01F 1/36; H01F 1/0063; C08F 2/26; G01N 2446/40
See application file for complete search history.

(56) References Cited

U.S. PATENT DOCUMENTS

| 3,926,789 | A  | * | 12/1975 | Shubert ...................... B03B 1/04 |
|           |    |   |         |                                 209/8  |
| 3,972,595 | A  | * | 8/1976  | Romankiw ............. G02F 1/091        |
|           |    |   |         |                                 359/228 |
| 4,873,102 | A  |   | 10/1989 | Chang et al. |
| 5,676,877 | A  |   | 10/1997 | Borduz et al. |
| 6,056,889 | A  |   | 5/2000  | Tsuda et al. |
| 6,866,838 | B1 |   | 3/2005  | Mondain-Monval et al. |
| 2003/0181606 | A1 | | 9/2003 | Ozaki et al. |
| 2004/0115433 | A1 | | 6/2004 | Elaissari et al. |
| 2005/0009002 | A1 | | 1/2005 | Chen et al. |
| 2005/0065288 | A1 | | 3/2005 | Ozaki et al. |
| 2008/0160277 | A1 | | 7/2008 | Tamori et al. |

FOREIGN PATENT DOCUMENTS

| CN | 101241130   | * | 8/2008  |
| EP | 2 660 268 A1 |   | 11/2013 |
| JP | 6-148189 A  |   | 5/1994  |
| JP | 7-94315 A   |   | 4/1995  |

(Continued)

OTHER PUBLICATIONS

Translation for CN 101241130, Aug. 13, 2008.*
International Search Report dated Aug. 22, 2017 in PCT/JP2017/019166 (with English translation), 5 pages.
Written Opinion of the International Searching Authority dated Aug. 22, 2017 in PCT/JP2017/019166 filed May 23, 2017, (with English translation), 9 pages.
Japanese Office Action dated Oct. 6, 2020 in Japanese Patent Application No. 2018-519558 (with English translation), 5 pages.
Extended European Search Report dated Dec. 4, 2019 in Patent Application No. 17802795.9, 7 pages.

(Continued)

*Primary Examiner* — C Melissa Koslow
(74) *Attorney, Agent, or Firm* — Oblon, McClelland, Maier & Neustadt, L.L.P.

(57) ABSTRACT

The present invention relates to composite particles, coated particles, a method of producing composite particles, a ligand-containing solid phase carrier, and a method of detecting or separating a target substance in a sample. The above described composite particles each contains an organic polymer and inorganic nanoparticles, wherein the content of the inorganic nanoparticles in the composite particles is more than 80% by mass, and wherein the composite particles have a volume average particle size of from 10 to 1,000 nm.

9 Claims, 2 Drawing Sheets

(56) References Cited

FOREIGN PATENT DOCUMENTS

| | | | |
|---|---|---|---|
| JP | 2003-509034 A | | 3/2003 |
| JP | 2004-205481 A | | 7/2004 |
| JP | 2004-528550 A | | 9/2004 |
| JP | 2004-533530 A | | 11/2004 |
| JP | 2006-275600 A | | 10/2006 |
| JP | 2006-292721 A | | 10/2006 |
| JP | 2008-164488 A | | 7/2008 |
| JP | 2008-241357 A | | 10/2008 |
| JP | 2008-258564 A | | 10/2008 |
| JP | 2008-309514 A | | 12/2008 |
| JP | 2010-91527 A | | 4/2010 |
| WO | WO 2015/062540 | * | 6/2015 |

OTHER PUBLICATIONS

Office Action as received in the corresponding CN patent application No. 201780031673.5 dated Jun. 28, 2021, w/computer generated English translation (Espacenet), 19 pages).
Office Action dated Apr. 27, 2021 in corresponding Japanese Patent Application No. 2018-519558 (with English Translation), 7 pages.

* cited by examiner

[FIG. 1]
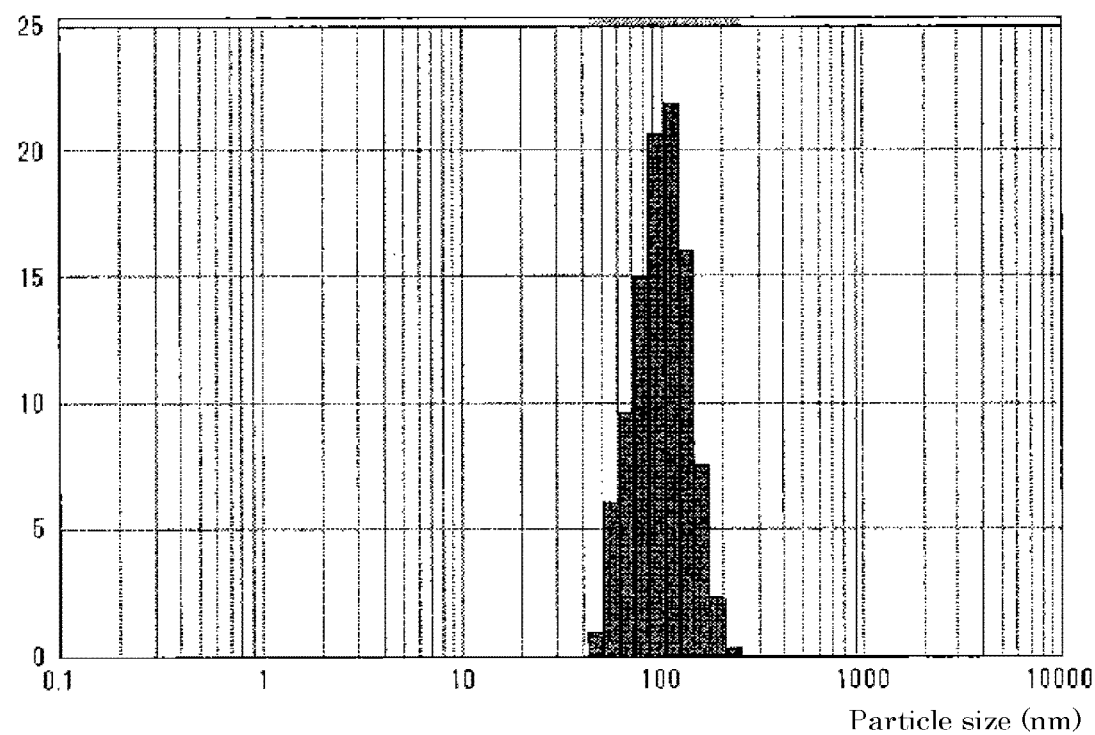

[FIG. 2]
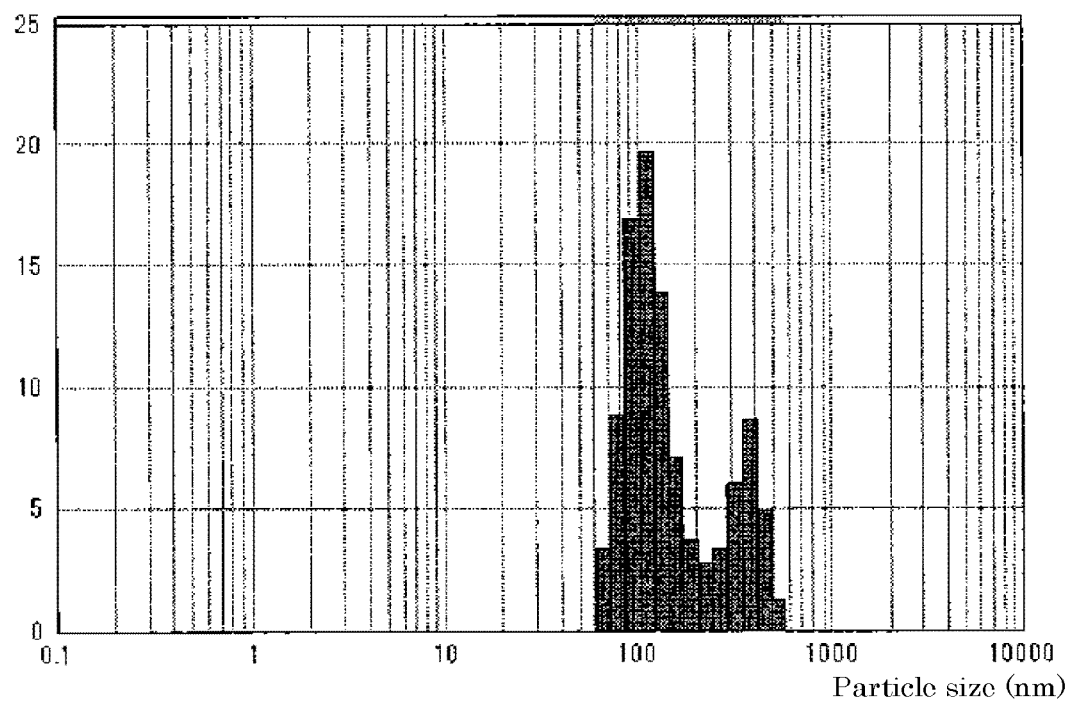

COMPOSITE PARTICLES, COATED PARTICLES, METHOD FOR PRODUCING COMPOSITE PARTICLES, LIGAND-CONTAINING SOLID PHASE CARRIER AND METHOD FOR DETECTING OR SEPARATING TARGET SUBSTANCE IN SAMPLE

TECHNICAL FIELD

The present invention relates to composite particles, coated particles, a method of producing composite particles, a ligand-containing solid phase carrier, and a method of detecting or separating a target substance in a sample.

BACKGROUND ART

In recent years, particles such as magnetic particles are actively applied, particularly, in the fields of, for example, diagnostic drugs and pharmaceutical researches, because of their ability to provide an excellent reaction field for, for example, an immunological reaction between an antigen and an antibody, or hybridization between DNAs or between DNA and RNA.

Magnetic particles having a small particle size are characterized in that they have a large surface area per unit mass, and thus capable of binding a large amount of biochemical substance. However, the use of such particles in an application as described above results in a longer time for performing magnetic separation; namely, the magnetic particles having a small particle size have a disadvantage in that they are poor in magnetic separation performance. In contrast, when it is intended to shorten the time required for magnetic separation, namely, when the magnetic separation performance is emphasized, magnetic particles having a large particle size, such as those described in Patent Document 1, should be used. However, in general, an increase in the particle size of magnetic particles leads to a decrease in the amount of biochemical substance bound per unit mass of the particles. In other words, it has been difficult to balance between increasing the amount of biochemical substance bound and realizing an excellent magnetic separation performance.

Since conventional magnetic particles have a low magnetic substance content, in particular, there have been problems, such as, for example, that the magnetic particles exhibit a low magnetic collection performance when formed to have a smaller particle size, and that magnetic separation cannot be performed in a state where the particles are dispersed in a liquid.

CITATION LIST

Patent Literature

Patent Literature 1: JP H6-148189 A

SUMMARY OF INVENTION

Technical Problem

One embodiment of the present invention provides composite particles which contain a high content of inorganic nanoparticles, such as particles of a magnetic substance.

Further, one embodiment of the present invention provides a method of producing composite particles, which method allows for the production of composite particles having a desired shape and excellent in magnetic separation performance even in the case of having a small particle size, easily and with a high production efficiency.

Solution to Problem

As a result of intensive studies to solve the above mentioned problems, the present inventors have found out that the composite particles having, for example, the following constitutions, allow for solving these problems, thereby completing the present invention.

Examples of the constitution of the present invention are as described below.

It is to be noted, in the present specification, that the description "A to B" which indicates, for example, a numerical range means "A or more and B or less", and includes A and B within the numerical range.

<1> Composite particles each including an organic polymer and inorganic nanoparticles,
wherein the content of the inorganic nanoparticles in the composite particles is more than 80% by mass, and
wherein the composite particles have a volume average particle size of from 10 to 1,000 nm.

<2> The composite particles according to <1>, wherein the composite particles have a coefficient of variation of the volume average particle size of 20% or less.

<3> The composite particles according to <1> or <2>, wherein the content of the inorganic nanoparticles is more than 80% by mass and 95% by mass or less.

<4> The composite particles according to any one of <1> to <3>, wherein the inorganic nanoparticles have a volume average particle size of from 5 to 25 nm.

<5> The composite particles according to any one of <1> to <4>, wherein the composite particles include at least one selected from the group consisting of a surfactant, an acid group-containing compound, an amino group-containing compound, a silane group-containing compound and a titanium atom-containing compound.

<6> The composite particles according to any one of <1> to <5>, wherein the inorganic nanoparticles are particles capable of being magnetized.

<7> The composite particles according to any one of <1> to <6>, wherein the inorganic nanoparticles include one kind or two or more kinds of inorganic materials selected from the group consisting of a simple substance of iron, titanium, cobalt, zinc, copper, manganese, nickel or gadolinium, an oxide thereof, or an alloy thereof; and a ferrite.

<8> The composite particles according to any one of <1> to <7>, wherein the inorganic nanoparticles are metal oxide particles.

<9> The composite particles according to any one of <1> to <8>, wherein the composite particles are magnetic particles.

<10> The composite particles according to any one of <1> to <9>, wherein the composite particles have surfaces to which at least one ligand can be physically adsorbed.

<11> The composite particles according to any one of <1> to <10>, wherein the composite particles have surfaces to which at least one ligand can be chemically bound.

<12> Coated particles including: the composite particles according to any one of <1> to <11>; and a polymer layer coating the composite particles.

<13> A method of producing composite particles, the method including the following steps (1) to (3):
step (1) of mixing a magnetic fluid, a monomer and a polymerization initiator to prepare a monomer mixed liquid;

step (2) of dispersing the monomer mixed liquid to prepare an emulsion; and step (3) of polymerizing the monomer in the emulsion.

<14> A ligand-containing solid phase carrier, which is a solid phase carrier selected from the composite particles according to any one of <1> to <11> and the coated particles according to <12>, and which includes a ligand.

<15> The ligand-containing solid phase carrier according to <14>, wherein the ligand is at least one selected from the group consisting of an antibody, an antigen, a nucleic acid, a nucleotide, a nucleoside, a protein, a peptide, an amino acid, a polysaccharide, a saccharide, a lipid, a vitamin, a drug, a substrate, a hormone and a neurotransmitter.

<16> The composite particles according to any one of <1> to <11>, the coated particles according to <12>, or the ligand-containing solid phase carrier according to <14> or <15>, which are/is for use in an immunoassay or for detecting a nucleic acid.

<17> A method of detecting or separating a target substance in a sample, the method using the ligand-containing solid phase carrier according to <14> or <15>.

Advantageous Effects of Invention

One embodiment of the present invention can provide composite particles which contain a high content of inorganic nanoparticles, such as particles of a magnetic substance. In particular, it is possible to provide composite particles in which agglomeration of inorganic nanoparticles is less likely to occur, despite the fact that the composite particles have a small volume average particle size as described above, and contain the inorganic nanoparticles at a high content.

Such composite particles can be suitably used as a support, a solid phase carrier or a medium, particularly in the fields of, for example, bioengineering, diagnosis, and pharmaceuticals, in which particles containing a high content of inorganic nanoparticles are required.

Further, one embodiment of the present invention provides a method which allows for the production of composite particles having a desired shape (for example, composite particles which are substantially spherical and in which the formation of agglomerates is prevented) and excellent in magnetic separation performance, easily and with a high production efficiency.

BRIEF DESCRIPTION OF DRAWINGS

FIG. 1 is a graph showing the particle size distribution of composite particles obtained in Example 1.

FIG. 2 is a graph showing the particle size distribution of composite particles obtained in Comparative Example 1.

DESCRIPTION OF EMBODIMENTS

<<Composite Particles>>

The composite particles according to one embodiment of the present invention are composite particles each containing an organic polymer and inorganic nanoparticles, wherein the content of the inorganic nanoparticles in the composite particles is more than 80° by mass, and wherein the composite particles have a volume average particle size of from 10 to 1,000 nm. In the present specification, the "composite particles" are not particularly limited, as long as they are particles each containing an organic polymer and inorganic nanoparticles. However, the composite particles are preferably particles in each of which inorganic nanoparticles are contained in an organic polymer, more preferably particles in each of which inorganic nanoparticles are dispersed in a matrix composed of an organic polymer, and particularly preferably magnetic particles.

The content of the inorganic nanoparticles in the composite particles according to one embodiment of the present invention is more than 80% by mass. The lower limit of the content of the inorganic nanoparticles is preferably 82% by mass, and more preferably 85% by mass, and the upper limit thereof is preferably 95% by mass, and more preferably 92% by mass.

It is preferred that the content of the inorganic nanoparticles be within the above described range, because the resulting composite particles can be more suitably used as a support, a solid phase carrier or a medium in the fields of, for example, bioengineering, diagnosis, and pharmaceuticals, and also because, when the composite particles are magnetic particles in which the inorganic nanoparticles are particles of a magnetic substance, it is possible to obtain composite particles excellent in magnetic separation performance and physical strength.

The composite particles according to one embodiment of the present invention have a volume average particle size (hereinafter, also simply referred to as "particle size") of from 10 to 1,000 nm, preferably from 50 to 700 nm, and more preferably from 80 to 600 nm.

When the composite particles have a particle size within the above described range, it is possible to easily obtain composite particles which have an excellent handleability and in which agglomeration of inorganic nanoparticles is less likely to occur, despite containing a high content of the inorganic nanoparticles.

When the particle size is less than 10 nm, the resulting composite particles have poor magnetic responsiveness, whereas when the particle size is more than 1,000 nm, the resulting composite particles have a smaller surface area per mass, resulting in poor reactivity or a decrease in the amount of biochemical substance bound.

Since the composite particles according to one embodiment of the present invention have a particle size within the above described range, when the composite particles according to one embodiment of the present invention are used, for example, in a diagnostic drug or a pharmaceutical research, it is possible to increase the amount of a ligand, preferably a biochemical substance (such as an antibody, an antibody fragment, a protein, a polypeptide, a polynucleotide, a nucleic acid, a nucleic acid fragment, or an enzyme) which can be bound per unit mass of the composite particles. In cases where the inorganic nanoparticles are particles of a magnetic substance, in particular, the composite particles exhibit an excellent magnetic separation performance, even in the case of having the above described particle size. As a result, it becomes possible to balance between increasing the amount of biochemical substance bound and achieving an excellent magnetic separation performance, which has hitherto been difficult.

The composite particles according to one embodiment of the present invention preferably have a coefficient of variation (CV value) of the particle size of 20% or less.

Having a CV value within the above described range is preferred, because it enables to easily obtain composite particles having smaller variations and capable of more easily exhibiting desired properties, and also because the time required for magnetic separation is less likely to vary, particularly in the case of composite particles containing a magnetic substance.

The particle size and the CV value can be measured, for example, using a dynamic light scattering particle size distribution measuring apparatus (Nanotrac UPA-EX150; manufactured by Nikkiso Co., Ltd.). Specifically, the CV value can be calculated according to the following Formula.

CV (%)=[standard deviation of particle size (σ)/ number average particle size ($D_n$)]×100

The composite particles according to one embodiment of the present invention are not particularly limited as long as the particles each contains an organic polymer and inorganic nanoparticles, and may contain components other than these. For example, in cases where a magnetic fluid is used in the production of the composite particles, the composite particles may contain any of conventionally known components contained in the magnetic fluid.

<Organic Polymer>

The organic polymer serves as a matrix of the composite particles according to one embodiment of the present invention.

A known polymer can be used as the organic polymer, and for example, a polymer obtained by polymerizing a monomer having an ethylenically unsaturated bond is preferred, but not particularly limited thereto. Examples of the monomer include styrene monomers, vinyl chloride, vinyl esters, unsaturated nitriles, (meth)acrylic acid esters and derivatives thereof.

More specific examples of the monomer include: styrene monomers such as styrene, α-methylstyrene, p-methylstyrene, p-chlorostyrene and chloromethylstyrene; vinyl chloride; vinyl esters such as vinyl acetate and vinyl propionate; unsaturated nitriles such as acrylonitrile; (meth)acrylic acid esters such as methyl (meth)acrylate, ethyl (meth)acrylate, butyl (meth)acrylate, 2-ethylhexyl (meth)acrylate, stearyl (meth)acrylate, ethylene glycol (meth)acrylate, trifluoroethyl (meth)acrylate, pentafluoropropyl (meth)acrylate, cyclohexyl (meth)acrylate and tetrahydrofurfuryl (meth) acrylate, and derivatives thereof; but not limited to these examples.

These monomers may be used alone, or two or more kinds thereof.

The organic polymer may contain a structural unit derived from a crosslinkable monomer, or may have a structure crosslinked by the structural unit. Examples of the crosslinkable monomer include divinylbenzene, ethylene glycol di(meth)acrylate, 1,6-hexanediol di(meth)acrylate, neopentyl glycol di(meth)acrylate, trimethylolpropane tri(meth) acrylate, tetramethylolmethane tri(meth)acrylate, tetramethylolpropane tetra(meth)acrylate, diallyl phthalate and isomers thereof, and triallyl isocyanurate; and derivatives thereof; but not limited to these examples.

These crosslinkable monomers may be used alone, or two or more kinds thereof.

The organic polymer is preferably a polymer containing a structural unit derived from a styrene monomer, because it allows for obtaining composite particles having, for example, an excellent dispersibility in an aqueous medium.

The content of the structural unit derived from a styrene monomer is preferably from 60 to 100% by mass, more preferably from 70 to 95% by mass, and still more preferably from 80 to 90% by mass with respect to 100% by mass of the total amount of the organic polymer contained in the composite particles, because it allows for obtaining composite particles having, for example, a more excellent dispersibility in an aqueous medium.

The organic polymer may contain, in addition to the structural unit derived from the monomer, a structural unit derived from a vinyl monomer containing a reactive functional group, since it is possible, for example, to easily obtain composite particles having surfaces to which at least one ligand can be chemically bound, specifically, composite particles capable of allowing, for example, an antigen, or an antibody to bind thereto via a reactive functional group.

The reactive functional group is preferably a group capable of binding, for example, an antigen, or an antibody by a covalent bond, and can be selected as appropriate depending on the desired application. Examples of the reactive functional group include a carboxyl group, a hydroxyl group, an epoxy group, an amino group, a triethylammonium group, a dimethylamino group and a sulfonic acid group. Examples of the vinyl monomer containing such a reactive functional group include (meth)acrylic acid, (meth)acrylic acid-2-hydroxyethyl, glycidyl (meth)acrylate, triethylammonium (meth)acrylate and dimethylamino (meth)acrylate, but not limited to these examples.

These vinyl monomers having such a reactive functional group may be used alone, or two or more kinds thereof.

The content of the organic polymer in the composite particles according to one embodiment of the present invention is not particularly limited, as long as the content of inorganic nanoparticles is within the above described range, and the organic polymer is contained in an amount sufficient for holding the inorganic nanoparticles. However, the content of the organic polymer is preferably less than 20% by mass, and the upper limit thereof is preferably 18% by mass, and particularly preferably 15° by mass; and the lower limit thereof is preferably 5° by mass, more preferably 8% by mass, and particularly preferably 10% by mass. Such a content is preferred because it allows for easily obtaining, for example, composite particles in which the inorganic nanoparticles are steadily held and which have an excellent physical strength; and also because, when the inorganic nanoparticles are particles of a magnetic substance, it allows for obtaining, for example, composite particles which are more excellent in magnetic separation performance.

<Inorganic Nanoparticles>

The material of the inorganic nanoparticles is preferably, but not particularly limited to, a material capable of being magnetized, and more preferably a magnetic substance. Specifically, it is preferred that the material be, for example, one kind or two or more kinds of inorganic materials selected from the group consisting of a simple substance of, for example, iron, titanium, cobalt, zinc, copper, manganese, nickel, or gadolinium, an oxide thereof, or an alloy thereof; and a ferrite. In particular, the material of the inorganic nanoparticles is preferably selected from: a metal oxide such as hematite, which is an iron oxide; a ferrite such as magnetic iron ore, manganese ferrite, nickel ferrite or manganese zinc ferrite; a cobalt alloy; and a nickel alloy, because it allows for obtaining, for example, composite particles which are more excellent in magnetic separation performance.

The material capable of being magnetized is preferably a material having superparamagnetism and having no residual magnetism, because it allows for obtaining, for example, composite particles which are more excellent in magnetic separation performance. The material having superparamagnetism is not particularly limited, and examples thereof include various types of ferrites such as triiron tetraoxide ($Fe_3O_4$) and γ-iron sesquioxide (γ-$Fe_2O_3$). In particular, a metal oxide is preferred, a metal oxide capable of being magnetized is more preferred, and triiron tetraoxide ($Fe_3O_4$) is particularly preferred.

As the magnetic substance, it is possible to use, for example, $Fe_3O_4$ which can be obtained by adding dropwise a mixed liquid containing $Fe^{2+}$ and $Fe^{3+}$ in a ratio of 1:2 to a basic solution, and allowing a coprecipitation reaction to occur. Further, a commercially available product, such as a magnetic substance contained in a magnetic fluid, for example, EMG 2001 (manufactured by Ferrotec Holdings Corporation) or Ferricolloid HC-50 (manufactured by Taiho Kozai Co., Ltd.) can also be used.

The particle size of the inorganic nanoparticles contained in the composite particles is preferably from 5 to 25 nm, more preferably from 5 to 20 nm, and still more preferably 8 to 15 nm, because it enables to obtain composite particles, for example, in which the inorganic nanoparticles are allowed to sufficiently exhibit their properties, and in particular, to obtain composite particles which are excellent in magnetic separation performance.

The lower limit of the dispersion diameter of the inorganic nanoparticles in the organic polymer is preferably 1 nm, and the upper limit thereof is preferably 30 nm. When the dispersion diameter is less than 1 nm, not only the production itself of the inorganic nanoparticles tends to become difficult, but also, in cases where the inorganic nanoparticles are particles of a magnetic substance, the resulting composite particles tend to have a lower magnetic responsiveness, and thus, a lower magnetic separation performance. When the dispersion diameter is more than 30 nm, on the other hand, and in cases where the inorganic nanoparticles are particles of a magnetic substance, not only residual magnetism is more likely to occur, making the particles prone to self-agglomeration, but also the magnetic substance is more likely to be exposed to the surfaces of the composite particles.

The lower limit of the dispersion diameter is more preferably 5 nm, and the upper limit thereof is more preferably 20 nm.

The dispersion diameter can be measured using a transmission electron microscope (TEM).

<Other Components>

The composite particles according to one embodiment of the present invention may contain, in cases where a magnetic fluid is used in the production of the composite particles, any of conventionally known components contained in the magnetic fluid, and any of conventionally known components used in the production of the composite particles, such as, for example, a surfactant. Such a conventionally known component may include, for example, but not limited to, a stabilizer such as a surfactant, and a compound other than the surfactant such as an acid group-containing compound, an amino group-containing compound, a silane group-containing compound and a titanium atom-containing compound.

Each type of stabilizer may be used alone, or two or more kinds thereof.

The surfactant is not particularly limited, and any of conventionally used compounds can be used as appropriate. Examples of the surfactant include: anionic surfactants such as oleic acid salts, carboxylic acid salts, sulfonic acid salts, sulfuric acid ester salts, and phosphoric acid ester salts; cationic surfactants such as amino acid salts and quaternary ammonium salts; nonionic surfactants including ester type surfactants such as glycerin fatty acid esters, ether type surfactants such as polyoxyethylene alkyl ethers and polyoxyethylene alkyl phenyl ethers, and ester-ether type surfactants such as fatty acid polyethylene glycols; and amphoteric surfactants such as alkyl betaine.

Examples of the acid group-containing compound include a compound containing a carboxyl group or a sulfo group disclosed in JP 2008-258564 A, and an inorganic acid, but not limited to these examples.

Examples of the amino group-containing compound include a fluorine-containing amine disclosed in JP H7-94315 A, but not limited thereto.

Examples of the silane group-containing compound include a silane group-containing surface treatment agent, and examples of the silane group-containing surface treatment agent include an alkoxysilane disclosed in JP H10-4006 A and a silane compound disclosed in JP 2004-205481 A, but not limited to these examples.

Examples of the titanium atom-containing compound include a titanium coupling agent, and examples of the titanium coupling agent include titanium triisostearoylisopropoxide, (2-n-butoxycarbonylbenzoyloxy)tributoxytitanium, titanium acetylacetonate, iso-butoxytitanium ethylacetoacetate, tetraisopropyl titanate and tetra-n-butyl titanate, but not limited to these examples.

It is preferred that the composite particles according to one embodiment of the present invention be composite particles having surfaces to which at least one ligand can be physically adsorbed, preferably composite particles having hydrophobic surfaces to which the ligand can be adsorbed by a hydrophobic interaction, or, composite particles having surfaces to which at least one ligand can be chemically bound, preferably composite particles having a reactive functional group capable of reacting with the ligand. This is because, for example, such composite particles can easily provide an excellent reaction field for, for example, an immunological reaction between an antigen and an antibody, or hybridization between DNAs or between DNA and RNA, and in particular, the particles can be easily used in, for example, a diagnostic drug, or a pharmaceutical research.

The composite particles having surfaces to which the ligand can be physically adsorbed can be obtained, for example, by using a monomer which allows the resulting organic polymer to be a hydrophobic polymer. The composite particles having surfaces to which the ligand can be chemically bound can be obtained, for example, by using a monomer containing a reactive functional group, when synthesizing the organic polymer.

The type of the ligand is not particularly limited, as long as the ligand has a moderate affinity to a target substance. Specific examples of the ligand include antibodies; antigens; nucleic acids such as DNA and RNA; nucleotides; nucleosides; proteins such as protein A, protein G, protein L, Fc-binding proteins, avidin, streptavidin, enzymes and lectins, and functional mutants thereof; peptides such as insulin; amino acids; saccharides and polysaccharides such as heparin, Lewis X and ganglioside; lipids; vitamins such as biotin; drugs; substrates; hormones; and neurotransmitters. Such a ligand may be used as a compound as it is; however, it is also possible to use a fragment of the compound, which can be obtained, for example, by subjecting the compound to an enzyme treatment or the like. Further, the ligand may be an artificially synthesized peptide or a peptide derivative, or a recombinant ligand.

A ligand suitable for separation or purification of an immunoglobulin may be, for example, a protein containing an immunoglobulin-binding domain, and the protein may contain a plurality of the same or different kinds of immunoglobulin-binding domains. The immunoglobulin-binding domain is preferably one kind or two or more kinds of immunoglobulin-binding domains selected from an immunoglobulin-binding domain of Protein A, an immunoglobulin-binding domain of protein G and an immunoglobulin-binding domain of protein L.

The ligand is preferably an antibody or an antigen, because, for example, it allows for easily obtaining a ligand-containing solid phase carrier suitable for, for example, a diagnostic drug.

The antibody or the antigen is not particularly limited, as long as it binds to a target substance. Examples thereof include: antibodies for coagulation/fibrinolysis-related tests, such as an anti-antiplasmin antibody, an anti-D dimer antibody, an anti-FDP antibody, an anti-tPA antibody, an anti-thrombin-antithrombin complex antibody and an anti-FPA antibody, or antigens against these antibodies; antibodies for tumor-related tests, such as an anti-BFP antibody, an anti-CEA antibody, an anti-AFP antibody, an anti-TSH antibody, an anti-ferritin antibody and an anti-CA19-9 antibody, or antigens against these antibodies; antibodies for serum protein-related tests, such as an anti-apolipoprotein antibody, an anti-$\beta$2-microglobulin antibody, an anti-al-microglobulin antibody, an anti-immunoglobulin antibody and an anti-CRP antibody, or antigens against these antibodies; antibodies for endocrine function tests, such as an anti-HCG antibody, or antigens against these antibodies; antibodies for drug analysis, such as an anti-digoxin antibody and an anti-lidocaine antibody, or antigens against these antibodies; antigens for infection-related tests, such as an HBs antigen, an HCV antigen, an HIV-1 antigen, an HIV-2 antigen, an HTLV-1 antigen, a *mycoplasma* antigen, a *Toxoplasma gondii* antigen and a streptolysin O antigen, or antibodies against these antigens; and antigens for autoimmune-related tests, such as a DNA antigen and heat-denatured human IgG, or antibodies against these antigens.

The antibody to be used as the ligand may be a polyclonal antibody or a monoclonal antibody.

<Method of Producing Composite Particles>

The method of producing composite particles according to one embodiment of the present invention is not particularly limited, and the composite particles can be produced, for example, by a method utilizing suspension polymerization, microsuspension polymerization, miniemulsion polymerization, or dispersion polymerization. In particular, a method utilizing miniemulsion polymerization is suitably used, since particles having a small particle size can be easily produced.

Further, the method of producing composite particles according to one embodiment of the present invention is more preferably a method including the following steps (1) to (3) (hereinafter, also referred to as the "present method"), because, for example, such a method allows for the production of composite particles having a desired shape (namely, composite particles which are substantially spherical and in which the formation of agglomerates is prevented) and excellent in magnetic separation performance, easily and with a high production efficiency.

Step (1): a step of mixing a magnetic fluid, a monomer and a polymerization initiator to prepare a mixture (hereinafter, referred to as "monomer mixed liquid") in the form of fluid.

Step (2): a step of dispersing the resulting monomer mixed liquid to prepare an emulsion.

Step (3): a step of polymerizing the monomer in the emulsion.

<Step (1)>

The step (1) is a step of mixing a magnetic fluid, a monomer and a polymerization initiator to prepare a monomer mixed liquid.

Since such a monomer mixed liquid is prepared in the step (1), and the thus prepared mixed liquid is used in the subsequent steps to produce composite particles, it is possible to produce composite particles containing a magnetic substance (inorganic nanoparticles) at a high content, particularly, at a content within the above described range, easily and with a high production efficiency. In particular, the use of the magnetic fluid in the step (1) enables to produce composite particles in a state where the magnetic substance contained in the fluid is uniformly dispersed. As a result, it is possible to easily produce composite particles in which the magnetic substance (inorganic nanoparticles) dispersed in the organic polymer has a dispersion diameter within the above described range, and to easily produce desired composite particles in which the agglomeration of the magnetic substance is prevented. Further, since the mixed liquid containing the monomer and the polymerization initiator is prepared in the step (1), the magnetic substance is uniformly dispersed in a matrix composed of the organic polymer, and the agglomeration of the magnetic substance is less likely to occur. As a result, it is possible to obtain composite particles having a high magnetic substance content of more than 80% by mass. Still further, since the agglomerates of the magnetic substance are less likely to be formed, the particle size and the shape of the composite particles can be easily controlled, making it possible to narrow the particle size distribution.

In contrast, in a conventional method of producing composite particles, a magnetic substance dispersion liquid is first prepared by dispersing a magnetic substance in an organic solvent, in order to, for example, disperse the magnetic substance at a predetermined dispersion diameter in the organic polymer. Specifically, water or an organic solvent, which is a liquid medium of magnetic fluid, is removed from the magnetic fluid to separate the magnetic substance, and another solvent is further added to the separated magnetic substance to prepare the magnetic substance dispersion liquid. To the resultant, a monomer, a polymerization initiator and a co-surfactant are added, to prepare a monomer mixed liquid.

However, as a result of intensive studies, the present inventors have found out that, in such a conventional production method, the particles of the magnetic substance agglomerate with each other to deteriorate the dispersion condition, when removing the liquid medium from the magnetic fluid, resulting in a failure to obtain composite particles containing a high content of the magnetic substance, easily and with a high production efficiency.

In another conventional method of producing composite particles, a monomer and a polymerization initiator are added to an emulsion containing a magnetic substance.

However, as a result of intensive studies, the present inventors have found out that, in such a conventional production method, particles having a shape other than a substantially spherical shape or agglomerates may be formed during the polymerization of the monomer, resulting in a failure to produce composite particles containing a high content of magnetic substance and having a desired shape, easily and with a high production efficiency.

Accordingly, it is preferred, in the present method, that a magnetic fluid be used as it is, without treating the magnetic fluid, for example, without carrying out a step of removing the liquid medium from the magnetic fluid, and that the fluid, a monomer and a polymerization initiator be mixed to prepare a monomer mixed liquid.

(Magnetic Fluid)

The magnetic fluid to be used in the step (1) contains inorganic nanoparticles.

The magnetic fluid usually contains: a magnetic substance (a) which is inorganic nanoparticles having a diameter of from several nm to several ten nm; a liquid (dispersion medium) (b) such as water, an organic solvent or an oil; and a stabilizer (c) for stably dispersing the magnetic substance in the dispersion medium.

In the magnetic fluid, a layer of a stabilizer such as a surfactant is usually present on the surface of the particles of the magnetic substance. Therefore, a repulsive force acts between the particles of the magnetic substance to prevent the agglomeration or precipitation, and the magnetic substance is retained in a stably dispersed state in the fluid. Further, the magnetic fluid is characterized in that it behaves as a normal liquid in the absence of a magnetic field, but when a magnetic field is applied, the viscosity of the liquid changes, and the magnetic fluid behaves as if the entire liquid is ferromagnetic. In addition, the magnetic fluid is also characterized in that the dispersed state of the inorganic nanoparticles, specifically, the dispersed state of the magnetic substance, in the fluid is retained even if an external force such as a magnetic field, gravity, or centrifugal force is applied from the outside, and therefore the magnetic fluid is attracted to a magnet, despite being a liquid.

As the magnetic substance (a) which has a diameter of from several nm to several ten nm, it is possible to use any of the above described magnetic substance materials having a diameter of from several nm to several ten nm, preferably particles thereof having a particle size of from 5 to 25 nm. Preferred particles (for example material (s), and particle size thereof) are also the same as those described above in the section of the inorganic nanoparticles.

The magnetic substance may be used alone, or two or more kinds thereof.

The liquid (dispersion medium) (b) such as water, an organic solvent or an oil, is preferably a liquid in which the magnetic substance can be well dispersed, in which the magnetic substance does not dissolve, and which can be mixed with a monomer. The dispersion medium as described above is preferably an organic solvent, and the organic solvent suitably contains an aliphatic hydrocarbon solvent. The aliphatic hydrocarbon solvent is suitably a linear or branched compound having from 5 to 20 carbon atoms, and more suitably a linear or branched compound having from 5 to 7 carbon atoms, because the magnetic substance can be particularly well dispersed therein. Specific examples thereof include pentane, hexane, heptane, isobutene and isopentane, but not limited to these examples.

The dispersion medium may be used alone, or two or more kinds thereof.

The content of the aliphatic hydrocarbon solvent in the organic solvent is preferably 80% by mass or more. When the content of the aliphatic hydrocarbon solvent is 80% by mass or more, the magnetic substance can be well dispersed in the resulting organic solvent, and it is possible to prevent the agglomeration of the magnetic substance in the composite particles according to one embodiment of the present invention, and to reduce variations in the content of the magnetic substance in the composite particles according to one embodiment of the present invention.

The content of the organic solvent in the magnetic fluid is such that the lower limit thereof is preferably 20 parts by mass, and the upper limit thereof is preferably 500 parts by mass, with respect to 100 parts by mass of the magnetic substance. When the content of the organic solvent is less than 20 parts by mass, there are cases where the magnetic substance cannot be sufficiently dispersed; whereas when the content is more than 500 parts by mass, removal of the residual solvent may be required after the step (3) described below, possibly making the operation of producing the composite particles complicated. The lower limit of the content of the organic solvent is more preferably 30 parts by mass, and the upper limit thereof is more preferably 300 parts by mass.

As the stabilizer (c) for stably dispersing the magnetic substance in the dispersion medium, a stabilizer conventionally used in a magnetic fluid can be used as appropriate. Examples thereof include the same stabilizers as those described in the section of other components of the composite particles.

Each type of stabilizer may be used alone, or two or more kinds thereof. For example, the magnetic fluid preferably contains at least one selected from the group consisting of a surfactant, an acid group-containing compound, an amino group-containing compound, a silane group-containing compound and a titanium atom-containing compound.

(Monomer)

Examples of the monomer to be used in the step (1) include the same monomers as those described above to be used in the synthesis of the organic polymer, and the same applies to the preferred monomers.

These monomers may be used alone, or two or more kinds thereof.

The amount of the monomer to be used is not particularly limited, however, it is preferred that the monomer is used in such an amount that the content of the inorganic nanoparticles (magnetic substance) in the resulting composite particles is within the above described range. Specifically, the amount of the monomer used is preferably from 1 to 100 parts by mass, more preferably from 3 to 50 parts by mass, still more preferably 5 parts by mass or more, particularly preferably 10 parts by mass or more, and still further preferably less than 20 parts by mass, with respect to 100 parts by mass of the magnetic substance in the magnetic fluid.

When the monomer is used in such an amount, it is possible to easily obtain composite particles in which the content of the inorganic nanoparticles (magnetic substance) is within the above described range, and which are excellent in magnetic separation performance and physical strength.

(Polymerization Initiator)

The polymerization initiator to be used in the step (1) is preferably a thermal radical polymerization initiator. Examples thereof include: azo initiators such as 2,2'-azobisisobutyronitrile, 2,2'-azobis-(2-methylpropanenitrile), 2,2'-azobis-(2,4-dimethylpentanenitrile), 2,2'-azobis-(2-methylbutanenitrile), 1,1'-azobis-(cyclohexanecarbonitrile), 2,2'-azobis-(2,4-dimethyl-4-methoxyvaleronitrile), 2,2'-azobis-(2,4-dimethylvaleronitrile) and 2,2'-azobis-(2-amidinopropane) hydrochloride; and peroxide-type radical polymerization initiators such as benzoyl peroxide, cumene hydroperoxide, hydrogen peroxide, acetyl peroxide, lauroyl peroxide, persulfate salts (such as ammonium persulfate) and peroxide esters (such as t-butyl peroctate and α-cumyl peroxypivalate); but not limited to these examples.

These polymerization initiators may be used alone, or two or more kinds thereof.

The amount of the polymerization initiator to be used is not particularly limited, but is preferably from 0.1 to 30 parts by mass, more preferably from 0.5 to 20 parts by mass, and still more preferably from 1 to 10 parts by mass, with respect to 100 parts by mass of the monomer.

The order of mixing the magnetic fluid, the monomer and the polymerization initiator is not particularly limited, and a surfactant may be used as necessary, when mixing these components.

<Step (2)>

The step (2) is a step of dispersing the monomer mixed liquid to prepare an emulsion. In the step (2), the monomer mixed liquid is preferably dispersed in an aqueous medium in which a surfactant is dissolved.

The aqueous medium is not particularly limited, and water such as distilled water or ion exchanged water is usually used.

The aqueous medium as used herein refers to a medium in which water accounts for at least 50% by mass or more.

The surfactant is not particularly limited, and any of an anionic surfactant, a cationic surfactant and a nonionic surfactant can be used. In particular, an anionic surfactant is suitably used.

The surfactant may be used alone, or two or more kinds thereof.

The anionic surfactant is not particularly limited, and examples thereof include sodium salts, potassium salts and ammonium salts of, for example, dodecylsulfuric acid, dodecylbenzenesulfuric acid, decylbenzenesulfuric acid, undecylbenzenesulfuric acid, tridecylbenzenesulfuric acid, or nonylbenzenesulfuric acid.

The cationic surfactant is not particularly limited, and examples thereof include cetyl trimethylammonium bromide, hexadecylpyridinium chloride, and hexadecyltrimethylammonium chloride.

The nonionic surfactant is not particularly limited, and examples thereof include polyvinyl alcohol. Further, it is possible to use, as the nonionic surfactant, any of commercially available products, such as, for example: Triton X-100, X-114, X-305 and N-101 (all of the above are manufactured by Union Carbide Corporation); Tween 20, 40, 60, 80 and 85 (all of the above are manufactured by ICI Americas, Inc.); Brij 35, 58, 76 and 98 (all of the above are manufactured by ICI Americas, Inc.); Nonidet P-40 (manufactured by Shell Chemicals); and Igepol C0530, C0630, C0720 and C0730 (manufactured by Rhone-Poulenc S.A.).

As the surfactant, it is also possible to use a reactive surfactant containing a reaction group which is polymerizable with the monomer. For example, an ethylenically unsaturated group such as vinyl group, allyl group or (meth) acryloyl group is suitable as the reaction group.

The amount of the surfactant to be used is not particularly limited, but is preferably from 0.01 to 100 parts by mass, and more preferably from 0.1 to 5 parts by mass, with respect to 100 parts by mass of the monomer mixed liquid, because, for example, it allows for easily preparing an emulsion.

The monomer mixed liquid can be dispersed, for example, by a method in which the monomer mixed liquid is added to an aqueous medium containing a surfactant, and the resulting mixture is emulsified using a shear mixing apparatus capable of generating a high shearing force.

The shear mixing apparatus is not particularly limited, and examples thereof include: batch type emulsifiers such as a homogenizer (manufactured by IKA Works, Inc.), Physcotron (manufactured by Microtec Co., Ltd.), Polytron (manufactured by Kinematica AG), and TK Autohomomixer (manufactured by Tokusyu Kika Kogyo); continuous emulsifiers such as Ebara Milder (manufactured by Pacific Machinery & Engineering Co., Ltd), TK Filmix and TK Pipeline Homomixer (manufactured by Tokusyu Kika Kogyo), Colloid Mill (manufactured by Kobelco Eco-Solutions Co., Ltd.), Crea Mix (manufactured by M Technique Co., Ltd.), Slasher and Trigonal wet pulverizers (manufactured by Nippon Coke & Industry Co., Ltd.), Cavitron (manufactured by Eurotech Co., Ltd.) and Fine Flow Mill (manufactured by Pacific Machinery & Engineering Co., Ltd); high pressure emulsifiers such as Microfluidizer (manufactured by Mizuho Industrial Co., Ltd.), Nanomizer (manufactured by Nanomizer Inc.) and APV Gaulin (manufactured by Gaulin Corporation); membrane emulsifiers such as a membrane emulsifier (manufactured by Reika Kogyo K.K.); vibration emulsifiers such as VibroMixer (manufactured by Reika Kogyo K.K.); and ultrasonic emulsifiers such as Ultrasonic Homogenizer (manufactured by Branson Ultrasonics Corporation). In particular, a probe-type ultrasonic disperser is suitably used.

In the step (2), it is preferred that the monomer mixed liquid be dispersed such that the particle size of the droplets in the resulting emulsion is about the same as the particle size of the desired composite particles, in order to obtain the same effect as described above. Specifically, it is preferred that the monomer mixed liquid be dispersed so as to obtain an emulsion containing droplets having the same particle size as that of the composite particles (the same applies to the preferred range thereof).

To disperse the monomer mixed liquid in the above described manner, in the case of using an ultrasonic disperser, for example, the monomer mixed liquid is dispersed under the conditions such that the lower limit of ultrasonic wave output is preferably 5 W, and the upper limit thereof is preferably 200 W. An output of ultrasonic wave of less than 5 W may result in the formation of large droplets due to insufficient dispersive force, possibly making the polymerization reaction in the step (3) difficult; whereas an output of ultrasonic wave of more than 200 W may result in a failure to obtain desired composite particles.

Further, the period of time for irradiating ultrasonic waves, for a single irradiation, is preferably within the range of from 10 seconds to 10 minutes, more preferably within the range of from 30 seconds to 5 minutes, and still more preferably within the range of from 1 minute to 3 minutes, although it varies depending on the ultrasonic wave output.

The irradiation of ultrasonic waves may be carried out once, or a plurality of times.

<Step (3)>

The step (3) is a step of polymerizing the monomer in the emulsion. This step allows for obtaining composite particles.

The conditions for the polymerization may be selected as appropriate, depending on, for example, the monomer to be used. In general, the polymerization is usually carried out by heating the emulsion at a temperature of from 50 to 95° C. for from 5 to 24 hours.

It is to be noted that, in a conventional method of producing composite particles, composite particles varying in the content of the magnetic substance are produced, and therefore, it is necessary to carry out a step of fractionating and collecting the composite particles having a desired magnetic substance content, after the polymerization of the monomer. However, the present method enables to produce composite particles in which the content of the magnetic substance is substantially constant, and thus allows for easily preparing composite particles containing the magnetic substance at a high content, without requiring the step of fractionating the particles. Accordingly, it can be said that the present method is a method excellent in productivity.

<Other Steps>

The present method may include other steps in addition to the steps (1) to (3), if necessary.

Examples of the other steps include a step of washing a dispersion liquid of the composite particles obtained in the step (3) with, for example, water by a magnetic separation method.

<<Coated Particles>>

The coated particles according to one embodiment of the present invention include: the composite particles according to one embodiment of the present invention; and a polymer layer coating the composite particles. The composite particles according to one embodiment of the present invention can be used, as they are, in a various types of applications. However, in order to modify the surfaces of the composite particles suitable for a desired application, it is preferred that the composite particles be coated with a polymer layer.

The polymer layer can be formed, for example, by carrying out (co-)polymerization of a (co-)polymerizable monomer in the presence of the composite particles, in a liquid, and if necessary, in the presence of a polymerization initiator, an emulsifying agent, a dispersant, a surfactant, an electrolyte, a crosslinking agent and/or a molecular weight adjusting agent. The formation of a polymer layer as described above is preferred, since it enables to easily produce coated particles having desired surface properties, such as, for example, that a desired functional group can be introduced to the surface of the polymer layer. Further, after the formation of the polymer layer, it is possible to modify the functional group (s) which can be present on the coated particle surface, by a method such as alkaline hydrolysis of an ethylenically unsaturated carboxylic acid alkyl ester, or alkaline saponification of a vinyl ester.

Further, the formation of the polymer layer may be carried out twice or more. In other words, the coated particles may include two or more polymer layers.

In cases where the polymer layer is formed as described above, the method of bringing the composite particles in contact with a (co-)polymerizable monomer is not particularly limited. For example, the contact can be achieved by a method in which the (co-)polymerizable monomer is added to the composite particles or a dispersion liquid of the composite particles, by any of a batch method, a sequential method, or a continuous method.

The polymerization conditions may be selected as appropriate, depending on, for example, the monomer, and the polymerization initiator to be used. However, polymerization is preferably carried out at a polymerization temperature of usually from 10 to 90° C., and preferably from 30 to 85° C., for a polymerization time of usually from 1 to 30 hours.

Depending on the content of the inorganic nanoparticles in the coated particles, the coated particles can be made more suitable for use as a support, a solid phase carrier or a medium in the fields of, for example, bioengineering, diagnosis, or pharmaceuticals. In cases where the inorganic nanoparticles are particles of a magnetic substance, the content of the inorganic nanoparticles in the coated particles is preferably from 1 to 95% by mass, more preferably from 35 to 95% by mass, and still more preferably from 45 to 95% by mass, because, for example, it allows for obtaining coated particles excellent in magnetic separation performance.

A vinyl polymer is preferred as a component of the polymer layer, but not particularly limited thereto. Examples of a vinyl monomer to be used in the synthesis of the vinyl polymer include: aromatic vinyl monomers such as styrene, α-methylstyrene, halogenated styrene and divinylbenzene; vinyl esters such as vinyl acetate and vinyl propionate; unsaturated nitriles such as acrylonitrile; ethylenically unsaturated carboxylic acid esters such as methyl (meth) acrylate, ethyl (meth)acrylate, butyl (meth)acrylate, 2-ethylhexyl (meth)acrylate, lauryl (meth)acrylate, ethylene glycol di(meth)acrylate and cyclohexyl (meth)acrylate; and acrolein; but not limited to these examples.

The vinyl polymer may be a homopolymer, or a copolymer of two or more types of monomers.

Further, the polymer layer may be a layer comprising a copolymer of the vinyl monomer and a monomer copolymerizable with the vinyl monomer. Examples of the monomer copolymerizable with the vinyl monomer include: conjugated diolefins such as butadiene and isoprene; mono- and di-carboxylic acid compounds and acid anhydrides thereof such as (meth)acrylic acid, itaconic acid, maleic anhydride and crotonic acid; and monomers such as (meth)acrylamide, glycidyl (meth)acrylate, N-methylol (meth)acrylamide, N-isopropyl (meth)acrylamide, 2-hydroxyethyl (meth)acrylate, glycerol mono(meth)acrylate, (meth)acrylates including as a side chain polyethylene glycol or polypropylene glycol having from 2 to 40 repeating units, diallyl phthalate, allyl (meth)acrylate, trimethylolpropane tri(meth)acrylate, styrene sulfonic acid and sodium salts thereof, 2-acrylamide-2-methylpropanesulfonic acid and sodium salts thereof, and isoprenesulfonic acid and sodium salts thereof.

Further, the polymer layer may contain, in addition to a structural unit derived from the monomer, a structural unit derived from a vinyl monomer containing a reactive functional group.

The reactive functional group is preferably a group capable of binding, for example, an antigen, or an antibody by a covalent bond, and may be selected as appropriate depending on the desired application. Examples of the reactive functional group include a carboxyl group, a hydroxyl group, an epoxy group, an amino group, a triethylammonium group, a dimethylamino group, and a sulfonic acid group.

Examples of the vinyl monomer containing such a reactive functional group include (meth)acrylic acid, (meth) acrylic acid-2-hydroxyethyl, glycidyl (meth)acrylate, triethylammonium (meth)acrylate and dimethylamino (meth) acrylate, but not limited to these examples.

These vinyl monomers containing a reactive functional group may be used alone, or two or more kinds thereof.

The content (thickness) of the polymer layer is not particularly limited, and is preferably such an amount that content of the inorganic nanoparticles in the coated particles is within the above described range.

The polymerization initiator is preferably an oil-soluble polymerization initiator, from the viewpoint of solubility in water. The use of a water-soluble polymerization initiator tends to result in the formation of a large amount of new particles consisting solely of a polymer layer and containing no composite particles, but not in the polymerization on the surfaces of the composite particles.

Examples of the oil-soluble polymerization initiator include peroxide or azo compounds such as benzoyl peroxide, lauroyl peroxide, t-butylperoxy 2-ethylhexanate, di(3, 5,5-trimethylhexanoyl) peroxide and azobisisobutyronitrile, but not limited to these examples.

The polymerization initiator may be used alone, or two or more kinds thereof.

The amount of the polymerization initiator to be used is preferably from 0.01 to 8 parts by mass, with respect to 100 parts by mass of the monomer.

As the emulsifying agent, for example a commonly used anionic surfactant, and/or nonionic surfactant can be used.

The emulsifying agent may be used alone, or two or more kinds thereof.

Examples of the anionic surfactant include alkali metal salts of higher alcohol sulfuric acid esters, alkali metal salts of alkylbenzenesulfonic acids, alkali metal salts of succinic acid dialkyl ester sulfonic acids, alkali metal salts of alkyl diphenyl ether disulfonic acids, sulfuric acid ester salts of polyoxyethylene alkyl (or alkyl phenyl) ethers, phosphoric acid ester salts of polyoxyethylene alkyl (or alkyl phenyl) ethers, and formalin condensate of sodium naphthalenesulfonate. Examples thereof also include Latemul S-180A (manufactured by Kao Corporation), Eleminol JS-2 (manufactured by Sanyo Chemical Industries, Ltd.), Aqualon HS-10 (manufactured by Dai-ichi Kogyo Seiyaku Co., Ltd.) and Adeka Reasoap SE-10N (manufactured by Adeka Corporation), but not limited to these examples.

Further, examples of the nonionic surfactant include polyoxyethylene alkyl ethers and polyoxyethylene alkyl phenyl ethers. Examples thereof also include Aqualon RS-20 (manufactured by Dai-ichi Kogyo Seiyaku Co., Ltd.) and Adeka Reasoap NE-20 (manufactured by Adeka Corporation).

It is preferred that the coated particles be coated particles having surfaces to which at least one ligand can be physically adsorbed, preferably coated particles having hydrophobic surfaces to which at least one ligand can be adsorbed by a hydrophobic interaction, or coated particles having surfaces to which at least one ligand can be chemically bound, preferably coated particles having a reactive functional group capable of reacting with a ligand; and the coated particles may contain, in addition to a structural unit derived from the monomer, a structural unit derived from a vinyl monomer containing a reactive functional group. This is because, for example, such coated particles can easily provide an excellent reaction field for, for example, an immunological reaction between an antigen and an antibody, or hybridization between DNAs or between DNA and RNA, and in particular, the particles can be easily used in, for example, a diagnostic drug, or a pharmaceutical research.

<<Ligand-Containing Solid Phase Carrier>>

The ligand-containing solid phase carrier according to one embodiment of the present invention is the composite particles having a ligand or the coated particles having a ligand, and is a carrier obtained by binding a ligand to a solid phase carrier selected from the composite particles and the coated particles.

Examples of the ligand include the same ligands as those described above in the section of the composite particles. Among these, an antibody or an antigen is preferred, because, for example, it allows for easily obtaining a ligand-containing solid phase carrier suitable for, for example, a diagnostic drug.

The ligand may be used alone, or of two or more kinds.

The binding of the ligand may be carried out in accordance with a conventional method, but is preferably carried out by a covalent binding method. For example, in cases where the reactive functional group is a carboxyl group and the ligand contains an amino group, a dehydration condensation agent may be used to carry out the binding.

<Applications>

The composite particles, the coated particles and the ligand-containing solid phase carrier according to one embodiment of the present invention can be widely used in researches, for example, in the fields of in vitro diagnosis and biochemistry, and suitably used, for example, as a support, a solid phase carrier or a medium in the field of bioengineering, diagnosis and pharmaceuticals. Specifically, the composite particles, the coated particles and the ligand-containing solid phase carrier can be suitably used as a means for separating and/or detecting a specimen such as an antigen, an antibody, a biomolecule, or a nucleic acid, and is particularly suitable for immunoassay and for detecting a nucleic acid.

In such applications, the composite particles or the coated particles according to one embodiment of the present invention may be used as they are, or alternatively, the ligand-containing solid phase carrier obtained by binding the ligand to the composite particles or the coated particles according to one embodiment of the present invention may be used.

More specifically, an antigen or an antibody such as a protein may be bound to the composite particles or the coated particles according to one embodiment of the present invention, to quantitatively or qualitatively analyze an object to be measured, by an antigen-antibody reaction between the bound antigen or the antibody and an antibody or an antigen as the object to be measured. An antibody may be bound to the composite particles or the coated particles according to one embodiment of the present invention, and an antigen such as a virus, a bacterium, a cell, a hormone or a chemical substance such as or a dioxin, may be allowed to bind to the antibody, to collect and concentrate the antigen. A nucleic acid analog such as DNA may be bound to the composite particles or the coated particles according to one embodiment of the present invention, to collect or detect a nucleic acid utilizing the hybridization of nucleic acids, or to collect or detect a chemical substance such as a protein or a pigment which binds to the bound nucleic acid. Avidin or biotin may be bound to the composite particles or the coated particles according to one embodiment of the present invention to collect or detect a molecule having biotin or avidin. An antibody or an antigen may be bound to the composite particles or the coated particles according to one embodiment of the present invention to carry out an enzyme immunoassay using a colorimetric method or a chemiluminescence method.

Further, by using the composite particles, the coated particles or the ligand-containing solid phase carrier according to one embodiment of the present invention, the analysis of conventional diagnostic items which have been performed using, for example, a 96-well plate as a carrier, can be carried out by an autoanalyzer utilizing magnetism, instead of the 96-well plate. Examples of a substance to be diagnosed include: proteins derived from living bodies; hormones such as luteinizing hormone and thyroid-stimulating hormone; various types of cancer cells; proteins which serve as cancer markers, such as prostate specific markers and bladder cancer markers; viruses such as hepatitis B virus, hepatitis C virus and herpes simplex virus; bacteria such as *Neisseria gonorrhoeae* and MRSA; fungi such as *Candida* and *Cryptococcus*; protozoa and parasites such as *Toxoplasma gondii*; proteins and nucleic acids which are components of, for example, these viruses, bacteria, fungi, protozoa, or parasites; environmental pollutants such as dioxins; and chemical substances such as pharmaceuticals including antibiotics and antiepileptic drugs.

<Method of Detecting or Separating Target Substance>

The method of detecting or separating a target substance in a sample, according to one embodiment of the present invention, uses the ligand-containing solid phase carrier.

The target substance is a substance which binds to a ligand. Specific examples of the target substance include antigens; antibodies such as monoclonal antibodies and polyclonal antibodies; cells (normal cells, and cancer cells such as colon cancer cells and circulating cancer cells); nucleic acids such as DNA and RNA; and bio-related substances such as proteins, peptides, amino acids, saccharides, polysaccharides, lipids and vitamins. The target substance may be a drug which is a potential drug target, or a small-molecule compound such as biotin. The target substance may also be labeled by, for example, a fluorescent substance.

The sample may be any sample which contains the target substance or potentially contains the target substance. Specifically, the sample may be, for example, blood, blood plasma, blood serum, or a buffer solution containing the target substance.

The method of detecting or separating a target substance, according to one embodiment of the present invention, may be carried out in accordance with a conventional method, except for using the ligand-containing solid phase carrier. For example, a method can be used which includes: a step of bringing the ligand-containing solid phase carrier into contact with a sample containing a target substance, by, for example, mixing (contact step); and a step of separating the ligand-containing solid phase carrier which has captured the target substance from the sample, using, for example, a magnet (separation step). Further, the above described method may also include, after the separation step, a step of detecting the target substance, or a step of dissociating the target substance from the ligand.

EXAMPLES

The present invention will now be described in detail by way of Examples. However, the present invention is in no way limited by these Examples. Respective analysis conditions in the Examples are as described below.

The volume average particle size of dispersoids or particles contained in a solution in each of the following Examples and Comparative Examples was measured using a dynamic light scattering particle size distribution measuring apparatus (Nanotrac UPA-EX150; manufactured by Nikkiso Co., Ltd.). As examples of the measured results, the particle size distribution of composite particles obtained in Example 1 is shown in FIG. 1, and the particle size distribution of composite particles obtained in Comparative Example 1 is shown in FIG. 2. The particle size values shown in FIG. 1 and FIG. 2 are values of volume average particle size.

Further, the content of the magnetic substance in the composite particles obtained in each of the following Examples and Comparative Examples was measured using a differential-type differential thermal balance (TG-8120; manufactured by Rigaku Corporation) at 500° C.

As a magnetic fluid to be used in the following Examples and Comparative Examples, "EMG 2001" (containing 14.3 g of magnetic substance in 27.0 g of the magnetic fluid; a dispersion liquid is heptane, manufactured by Ferrotec Corporation) was used. No variation in the concentration of the magnetic substance was observed in the magnetic fluid, even when a magnetic field, gravity or centrifugal force was applied to the magnetic fluid, and the dispersed state of the magnetic substance in the magnetic fluid was retained. The dispersed state as described above can be determined by confirming the absence of precipitates and the absence of separation between the magnetic substance and the dispersion liquid, by visual observation.

Example 1

To 27.0 g of the magnetic fluid "EMG 2001", 1.35 g of styrene, 0.15 g of divinylbenzene and 0.06 g of 2,2'-azobisisobutyronitrile were added, followed by mixing to obtain a monomer mixed liquid. Subsequently, 75 g of an aqueous solution in which 0.75 g of sodium dodecyl sulfate was dissolved, was added to the thus obtained monomer mixed liquid. The resulting mixture was then subjected to an ultrasonic wave treatment (ultrasonic wave irradiation (at an ultrasonic wave output of 150 W) was performed for two minutes, and then the ultrasonic wave irradiation was stopped for two minutes) while cooling with ice, and using an ultrasonic homogenizer (US 300T; manufactured by Nihonseiki Kaisha Ltd.). The above described ultrasonic wave treatment was repeated 10 times, to prepare an emulsion in which the monomer mixed liquid containing the magnetic substance was dispersed in water. The volume average particle size of the droplets in the resulting emulsion was 104 nm.

Subsequently, the resulting emulsion was polymerized at 70° C. for seven hours, and then washed with water by magnetic separation, to obtain a dispersion liquid of composite particles A. The volume average particle size of the composite particles A in the thus obtained particle dispersion liquid was 103 nm, and the content of the magnetic substance in the composite particles A was 90% by mass. The thus measured value of the magnetic substance content coincides with the theoretical value thereof, and this reveals that the composite particles (the dispersion liquid thereof) have been obtained with a high production efficiency. It is to be noted that the theoretical value (% by mass) as used herein refers to a value based on the assumption that all of the magnetic substance, the monomers and the initiator charged were formed into the composite particles, and can be determined by the following equation: "amount of magnetic substance×100/(amount of magnetic substance+amounts of respective monomers+amount of initiator)". Further, the fact that the resulting composite particles exhibited a clustered particle size distribution, as shown in FIG. 1, reveals that the composite particles having a desired shape have been obtained with a high production efficiency.

Example 2

The same procedure as in Example 1 was carried out, except that 1.35 g of methyl methacrylate and 0.15 g of trimethylolpropane trimethacrylate (hereinafter, referred to as "TMP") were used as monomers, instead of 1.35 g of styrene and 0.15 g of divinylbenzene, to obtain composite particles B (a dispersion liquid thereof). The thus obtained composite particles B had a volume average particle size of 107 nm, and the content of the magnetic substance in the composite particles B was 89% by mass. The thus determined value of magnetic substance content differs from the theoretical value by 1% by mass, which is a slight difference, and this reveals that the composite particles (the dispersion liquid thereof) have been obtained with a high production efficiency.

Example 3

To a mixed solution obtained by mixing 1.2 g of methyl methacrylate, 0.3 g of TMP, 0.3 g of methacrylic acid and 0.1 g of di(3,5,5-trimethylhexanoyl) peroxide (Peroyl 355; manufactured by NOF Corporation), 30 g of an aqueous solution obtained by dissolving 0.15 g of sodium dodecyl sulfate was added, to prepare an emulsion c using an ultrasonic homogenizer (US 300T).

Into a separable flask, 73.5 g of the dispersion liquid of the composite particles A produced in Example 1 (containing 3.0 g of the composite particles A) was introduced. While controlling the temperature of the dispersion liquid to 60° C. in a water bath, the emulsion c was added thereto dropwise over two hours. After the completion of the dropwise addition, polymerization was carried out over one hour while maintaining the temperature at 60° C. Subsequently, the temperature was raised to 80° C., and maintained for two hours to complete the reaction. The resulting dispersion liquid was washed with water by magnetic separation, to prepare a dispersion liquid of coated particles C. The volume average particle size of the coated particles C in the thus obtained particle dispersion liquid was 109 nm, and the content of the magnetic substance in the coated particles C was 59% by mass.

Example 4

The same procedure as in Example 1 was carried out, except that sodium dodecyl sulfate was used in an amount of 0.3 g, and that the ultrasonic wave treatment was repeated four times, to prepare composite particles E (a dispersion liquid thereof). The resulting composite particles E had a volume average particle size of 232 nm, and the content of the magnetic substance in the composite particles E was 86% by mass.

Example 5

The same procedure as in Example 1 was carried out, except that the ultrasonic wave treatment was carried out by performing the ultrasonic wave irradiation for one minute (at an ultrasonic wave output of 150 W) followed by stopping the ultrasonic wave irradiation for one minute, and repeating this cycle of the ultrasonic wave treatment three times, to obtain composite particles F (a dispersion liquid thereof). The resulting composite particles F had a volume average particle size of 515 nm, and the content of the magnetic substance in the composite particles F was 88% by mass.

Example 6

The same procedure as in Example 1 was carried out, except that a colloid mill (magic LAB; manufactured by IKA Works, Inc.) was used, instead of the ultrasonic homogenizer (US 300T), to prepare an emulsion. The colloid mill was used under the treatment conditions of 25,000 rpm and 20 min. The volume average particle size of the droplets in the thus obtained emulsion was 110 nm.

Subsequently, polymerization was carried out in the same manner as in Example 1, to prepare composite particles G (a dispersion liquid thereof). The resulting composite particles G had a volume average particle size of 108 nm, and the content of the magnetic substance in the composite particles G was 89% by mass.

Example 7

A quantity of 10 mg of the composite particles A was dispersed in a boric acid buffer having a pH of 9.5, and 0.1 mL of a solution obtained by dissolving 0.2 mg of streptavidin was added thereto. The resulting mixture was stirred by rotation at 37° C. for 16 hours, and then washed four times with a Tris buffer, to prepare streptavidin-bound particles in which streptavidin had been immobilized on the surfaces of the composite particles A. The amount of streptavidin bound to the composite particles was measured by a bicinchoninic acid (BCA) assay, to be 20 µg per 1 mg of composite particles.

Example 8

A quantity of 10 mg of the coated particles C was dispersed in 1 mL of a 100 mM MES (2-morpholinoethanesulfonicacid, monohydrate) buffer having a pH of 5.0. To the resulting dispersion, 0.1 mL of a WSC solution obtained by dissolving 1-ethyl-3-dimethylaminopropyl carbodiimide hydrochloride (WSC, manufactured by Dojindo Laboratories) in a 100 mM MES buffer having a pH of 5.0 so as to achieve a concentration of 10 mg/mL, was added, and then stirred by rotation at room temperature for two hours. To the resultant, 0.1 mL of a 100 mM MES buffer having a pH of 5.0 and in which 0.2 mg of streptavidin was dissolved, was further added. The resulting mixture was stirred by rotation at room temperature for eight hours, followed by washing four times with a Tris buffer to remove unreacted streptavidin, to prepare streptavidin-bound particles in which streptavidin had been immobilized on the surfaces of the coated particles C. The amount of streptavidin bound to the coated particles was measured by the BCA assay, to be 18 µg per 1 mg of composite particles.

Example 9

The same procedure as in Example 3 was carried out, except that 1.2 g of glycidyl methacrylate and 0.3 g of methacrylic acid were used, instead of 1.2 g of methyl methacrylate, 0.3 g of TMP and 0.3 g of methacrylic acid used in the preparation of the emulsion c, and that 73.5 g of the dispersion liquid of the coated particles C produced in Example 3 (containing 1.5 g of the composite particles A) was used, instead of the dispersion liquid of the composite particles A, to prepare coated particles D (a dispersion liquid thereof). The resulting coated particles D had a volume average particle size of 165 nm, and the content of the magnetic substance in the coated particles D was 41% by mass.

The same procedure as in Example 8 was carried out except that the coated particles D were used instead of the coated particles C, to prepare streptavidin-bound particles. The amount of streptavidin bound to the coated particles was measured by the BCA assay, to be 17 µg per 1 mg of composite particles.

Comparative Example 1

A quantity of 27.0 g of the magnetic fluid "EMG 2001" was dried in an incubator at 80° C. for 12 hours, to obtain 17 g of a concentrated magnetic substance. To the thus obtained magnetic substance, 10 g of heptane was added, followed by stirring overnight, to obtain a magnetic substance dispersion liquid. When a magnet was brought into proximity of the resulting magnetic substance dispersion liquid to apply a magnetic field, the magnetic substance in the magnetic substance dispersion liquid was attracted to the magnet, and the dispersed state of the magnetic substance was not retained. Accordingly, the magnetic substance dispersion liquid was different from the magnetic fluid.

The same procedure as in Example 1 was carried out, except that the thus obtained magnetic substance dispersion liquid was used instead of the magnetic fluid "EMG2001" to prepare composite particles (a dispersion liquid thereof). The resulting composite particles exhibited a particle size distribution with two clusters, as shown FIG. 2. Further, the presence of agglomerates of the magnetic substance in the thus obtained dispersion liquid of the composite particles was confirmed by visual observation. The resulting composite particles had a volume average particle size of 177 nm, and the content of the magnetic substance in the composite particles was 68% by mass. The thus determined content of the magnetic substance differs from the theoretical value by 24% by mass, which is a great difference. In addition, the resulting composite particles exhibited a particle size distribution with two clusters, as shown in FIG. 2. This reveals that it has failed to produce composite particles (a dispersion liquid thereof) having a desired shape, with a high production efficiency.

It is to be noted that, since the magnetic substance dispersion liquid was different from the magnetic fluid, the method of producing composite particles according to Comparative Example 1 does not corresponds to the present method.

Comparative Example 2

A quantity of 27.0 g of the magnetic fluid "EMG 2001" was added to 75 g of an aqueous solution in which 0.75 g of sodium dodecyl sulfate was dissolved, to obtain a mixed liquid. The resulting mixed liquid was subjected to an ultrasonic wave treatment in the same manner as in Example 1, to prepare an emulsion in which the magnetic fluid was dispersed in water. The volume average particle size of the droplets in the resulting emulsion was 98 nm.

Subsequently, a mixed liquid of 1.35 g of styrene, 0.15 g of divinylbenzene and 0.06 g of 2,2'-azobisisobutyronitrile was added to the resulting emulsion. Thereafter, the resulting mixture was heated to 70° C., polymerized for seven hours, and then washed with water by magnetic separation, to obtain a composite particle dispersion liquid. The volume average particle size of the composite particles in the thus obtained composite particle dispersion liquid was 131 nm, and the content of the magnetic substance in the composite particles was 77% by mass. The thus determined content of the magnetic substance differs from the theoretical value by 13% by mass, which is a great difference. This reveals that it has failed to produce the composite particles (a dispersion liquid thereof) with a high production efficiency. It is to be noted that the agglomerates of the magnetic substance were present in the resulting composite particle dispersion liquid, and further, that composite particles having a deformed shape which is not spherical, and aggregates of the composite particles were also present in the composite particle dispersion liquid, in a mixed state.

The results of the composite particles (dispersion liquids thereof) obtained in the Examples and Comparative Examples are shown in the following Table 1. In the following Table 1, when the difference between the content of the magnetic substance in the resulting composite particles and the theoretical value thereof was 10% by mass or less, the production efficiency of the corresponding composite particles was evaluated as "○" (produced with an excellent production efficiency, and able to control the content of the magnetic substance). When the difference was more than 10° by mass, in contrast, the production efficiency was evaluated as "x" (produced with a poor production efficiency, and unable to control the content of the magnetic substance).

TABLE 1

|  | Volume average particle size (nm) | Magnetic substance content (% by mass) | Difference between magnetic substance content and theoretical value thereof (% by mass) | Presence or absence of deformed particles or aggregates | Production Efficiency |
|---|---|---|---|---|---|
| Example 1 | 103 | 90 | 0 | Absent | ○ |
| Example 2 | 107 | 89 | 1 | Absent | ○ |
| Example 4 | 232 | 86 | 4 | Absent | ○ |
| Example 5 | 515 | 88 | 2 | Absent | ○ |
| Example 6 | 108 | 89 | 1 | Absent | ○ |
| Comparative Example 1 | 177 | 68 | 24 | Present | x |
| Comparative Example 2 | 131 | 77 | 13 | Present | x |

As shown in Table 1, in each of Examples 1, 2, and 4 to 6, it was possible to produce composite particles having a high magnetic substance content and a volume average particle size of about from 100 to 500 nm, easily, stably, and with a high productivity.

On the other hand, in Comparative Example 1 in which no magnetic fluid was used, the magnetic substance was not dispersed uniformly, resulting in the formation of the agglomerates of the magnetic substance. In Comparative Example 2, the agglomerates of the magnetic substance were formed, and some of the resulting composite particles had a deformed shape which is not spherical, or formed into aggregates (mass) resulting from an uneven contact between the droplets in the emulsion and the monomers. Further, in each of Comparative Examples 1 and 2, it was unable to produce composite particles having a high magnetic substance content, and the production efficiency was significantly low.

Example 10

The dispersion liquid of the composite particles C was subjected to magnetic separation to remove the supernatant, and the resultant was then washed twice with a 0.1 M MES buffer (pH 5.5). After the washing, the resultant was subjected to magnetic separation to remove the supernatant. To the resultant, a 0.1 M MES buffer (pH 5.5) and an anti-PSA (prostate specific antigen) antibody solution were added such that the amount of antibody per 1 mg of the composite particles C was 10 μg. To the resultant, EDC (1-ethyl-3-dimethylaminopropyl carbodiimide hydrochloride (manufactured by Dojindo Laboratories, 3 mg/mL)) was further added such that the amount thereof per 1 mg of the composite particles C was 100 μg, followed by mixing by inversion at 25° C. for two hours. After the completion of the reaction, the resulting mixture was subjected to magnetic separation to remove the supernatant, and then washed twice with a Tris buffer/0.01° Triton X-100. Subsequently, the resultant was subjected to magnetic separation to remove the supernatant, and the buffer was replaced with a 50 mM Tris buffer, followed by further magnetic separation to remove the supernatant. Thereafter, the resulting particles were suspended in a BSA-containing buffer (a 50 mM Tris buffer containing 1% by weight of BSA, pH: 7.5), to obtain an antibody-bound particle dispersion liquid (composite particle concentration: 0.05% by weight).

A quantity of 25 µL of the thus prepared antibody-bound particle dispersion liquid was dispensed, and then 25 µL of a sample (human serum or a standard solution (PSA antigen-containing liquid: 0 to 1,000 µg/mL)) was dispensed into the dispensed antibody-bound particle dispersion liquid. Into the resultant, 25 µL of an ALP (alkaline phosphatase)-labeled anti-PSA antibody liquid was further dispensed, followed by a reaction at 25° C. for 20 minutes. After the reaction, magnetic separation was carried out to separate the particles, and the particles were washed using a 96-well plate washer (Hydro Flex; manufactured by Tecan Japan Co., Ltd.), with a Tris buffer/0.01% Triton X-100. Thereafter, an ALP substrate liquid (Lumipulse substrate liquid; manufactured by Fujirebio Inc.) was added thereto. The resulting mixture was allowed to react at 25° C. for five minutes, and the measurement of the emission intensity was carried out (using ARVO X5; manufactured by PerkinElmer Co., Ltd.)). The results are shown in Table 2.

The thus determined emission intensity was dependent on the antigen concentration and showed dilution linearity. This confirmed that the composite particles C can be used as a solid phase carrier for use in an immunoassay.

TABLE 2

| Antigen Concentration (pg/mL) | Emission Intensity |
| --- | --- |
| 0 | 225 |
| 10 | 347 |
| 25 | 498 |
| 50 | 782 |
| 100 | 1182 |
| 250 | 2595 |
| 500 | 4963 |
| 1000 | 10782 |

The invention claimed is:

1. A method of producing composite particles, the method comprising:
   mixing a magnetic fluid, a monomer and a polymerization initiator to prepare a monomer mixed liquid so that a content of magnetic nanoparticles is more than 80% by mass with respect to 100% by mass of a material for forming the composite particles in the monomer mixed liquid;
   dispersing the monomer mixed liquid to prepare an emulsion; and
   polymerizing the monomer in the emulsion to produce composite particles that comprise magnetic nanoparticles in an amount of more than 80% by mass.

2. The method of claim 1, wherein the composite particles have a volume average particle size of from 10 to 1,000 nm.

3. The method of claim 1, wherein the composite particles have a coefficient of variation of the volume average particle size of 20% or less.

4. The method of claim 1, wherein the magnetic nanoparticles are present in an amount of more than 80% by mass to 95% by mass.

5. The method of claim 1, wherein the magnetic nanoparticles have a volume average particle size of from 5 to 25 nm.

6. The method of claim 1,
   wherein the magnetic fluid comprises at least one selected from the group consisting of a surfactant, an acid group-containing compound, an amino group-containing compound, a silane group-containing compound and a titanium atom-containing compound, and
   wherein the composite particles comprise at least one selected from the group consisting of a surfactant, an acid group-containing compound, an amino group-containing compound, a silane group-containing compound and a titanium atom-containing compound.

7. The method of claim 1, wherein the magnetic nanoparticles are metal oxide particles.

8. The method of claim 1, wherein the monomer is a monomer such that the resulting polymer obtained is a hydrophobic polymer, and wherein the composite particles have surfaces to which at least one ligand can be physically adsorbed.

9. The method of claim 1, wherein the monomer is a monomer containing a reactive functional group, and wherein the composite particles have surfaces to which at least one ligand can be chemically bound.

* * * * *